United States Patent
Kasahara et al.

(10) Patent No.: US 10,565,698 B2
(45) Date of Patent: Feb. 18, 2020

(54) CIRCULAR SCRATCH INSPECTION APPARATUS

(71) Applicant: KAWASAKI JUKOGYO KABUSHIKI KAISHA, Kobe-shi, Hyogo (JP)

(72) Inventors: Kenji Kasahara, Gifu (JP); Shuhei Segawa, Aisai (JP); Osamu Ohji, Kako-gun (JP); Yuuki Hanawa, Akashi (JP); Shogo Kojima, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 63 days.

(21) Appl. No.: 15/794,848

(22) Filed: Oct. 26, 2017

(65) Prior Publication Data

US 2018/0114309 A1   Apr. 26, 2018

(30) Foreign Application Priority Data

Oct. 26, 2016 (JP) .................. 2016-209215

(51) Int. Cl.
| | |
|---|---|
| *G06K 9/00* | (2006.01) |
| *G06T 7/00* | (2017.01) |
| *G01N 21/88* | (2006.01) |
| *H04N 5/225* | (2006.01) |

(52) U.S. Cl.
CPC ....... *G06T 7/0004* (2013.01); *G01N 21/8851* (2013.01); *G06T 2207/30164* (2013.01); *G06T 2207/30242* (2013.01); *H04N 5/2256* (2013.01)

(58) Field of Classification Search
CPC . G06T 2207/20168; G06T 2207/30164; G06T 2207/30242; G06T 7/0004; G06T 7/0006; G06T 7/12; G06T 7/64; G01N 21/8851; H04N 5/2256
See application file for complete search history.

(56) References Cited

U.S. PATENT DOCUMENTS

| | | | |
|---|---|---|---|
| 6,256,091 B1* | 7/2001 | Kobayashi ............. | G01N 21/88 356/237.1 |
| 2006/0181700 A1* | 8/2006 | Andrews ................. | G01N 21/21 356/237.2 |
| 2015/0078650 A1* | 3/2015 | Sezginer ............ | G01N 21/8851 382/141 |

FOREIGN PATENT DOCUMENTS

| | | | | |
|---|---|---|---|---|
| JP | 2000-055824 | * | 2/2000 | ............. G01B 11/30 |
| JP | 2000-055824 A | | 2/2000 | |

* cited by examiner

*Primary Examiner* — Amara Abdi
(74) *Attorney, Agent, or Firm* — Oliff PLC

(57) ABSTRACT

A circular scratch inspection apparatus includes: a camera capturing an image of a workpiece surface around a hole; illumination device emitting light to the workpiece surface around the hole, the light being reflected on the workpiece surface is not directly incident on the camera; and image processor. The image processor: generates a second-derivative image by performing secondary differentiation on luminance values in an actual image obtained by the camera; generates a second-derivative curve for each of a plurality of ruler lines, extending radially from the hole center and are set in an inspection target region on the workpiece surface; counts a first reference number of times for each ruler line; calculates a first reference total number of times; and determines presence or absence of a circular scratch by using the first reference total number of times.

4 Claims, 2 Drawing Sheets

CIRCULAR SCRATCH INSPECTION APPARATUS

BACKGROUND OF THE INVENTION

1. Field of the Invention

The present invention relates to a circular scratch inspection apparatus.

2. Description of the Related Art

Conventionally, various inspection apparatuses for performing an inspection to check whether or not flaws are present on a workpiece surface have been proposed. For example, Japanese Laid-Open Patent Application Publication No. 2000-55824 discloses a flaw inspection apparatus, in which a camera is disposed in a direction normal to the workpiece surface and which is configured to emit light diagonally onto the workpiece surface, such that the light that is reflected regularly on the workpiece surface is not directly incident on the camera, but the light that is reflected irregularly on flaws on the workpiece surface is directly incident on the camera.

SUMMARY OF THE INVENTION

In the case of machining a hole in a workpiece by a drill, there are cases where swarf generated from the machining rotates together with the drill, and the rotating swarf forms circular scratches (arc-shaped or round flaws) on the workpiece surface around the hole. The flaw inspection apparatus disclosed in Japanese Laid-Open Patent Application Publication No. 2000-55824 is capable of performing an inspection to check whether or not flaws are present. However, this flaw inspection apparatus is not capable of determining whether or not the flaws are circular scratches.

In view of the above, an object of the present invention is to provide a circular scratch inspection apparatus capable of performing an inspection to check whether or not a circular scratch is present on a workpiece surface around a hole formed therein.

In order to solve the above-described problems, a circular scratch inspection apparatus according to the present invention includes: a camera that captures an image of a workpiece surface around a hole formed therein; at least one illumination device that emits light to the workpiece surface around the hole, such that the light that is reflected regularly on the workpiece surface is not directly incident on the camera; and an image processor that performs image processing on an actual image obtained by the camera. The image processor includes: a second-derivative image generator that generates a second-derivative image by performing secondary differentiation on luminance values in the actual image; a second-derivative curve generator that generates a second-derivative curve for each of a plurality of ruler lines, which extend radially from a center of the hole and which are set in an inspection target region on the workpiece surface, the second-derivative curve indicating change in second-derivative values on the ruler line in the second-derivative image; and a circular scratch determiner that counts a first reference number of times for each ruler line, the first reference number of times being the number of times the second-derivative curve crosses a first threshold on the ruler line, calculates a first reference total number of times, which is a sum of the first reference numbers of times of the plurality of ruler lines, and determines presence or absence of a circular scratch by using the first reference total number of times.

According to the above-described configuration, the presence or absence of a flaw on each ruler line can be detected based on the first reference number of times, which is the number of times the second-derivative curve crosses the first threshold on the ruler line. Moreover, whether or not the detected flaw is a circular scratch can be determined by using the first reference total number of times, which is the sum of the first reference numbers of times of the plurality of radially extending ruler lines. This makes it possible to perform an inspection to check whether or not a circular scratch is present around the hole formed in the workpiece surface.

The present invention makes it possible to perform an inspection to check whether or not a circular scratch is present on a workpiece surface around a hole formed therein.

The above and other objects, features, and advantages of the present invention will more fully be apparent from the following detailed description of a preferred embodiment with accompanying drawings.

DESCRIPTION OF THE PREFERRED EMBODIMENTS

Figure 1:
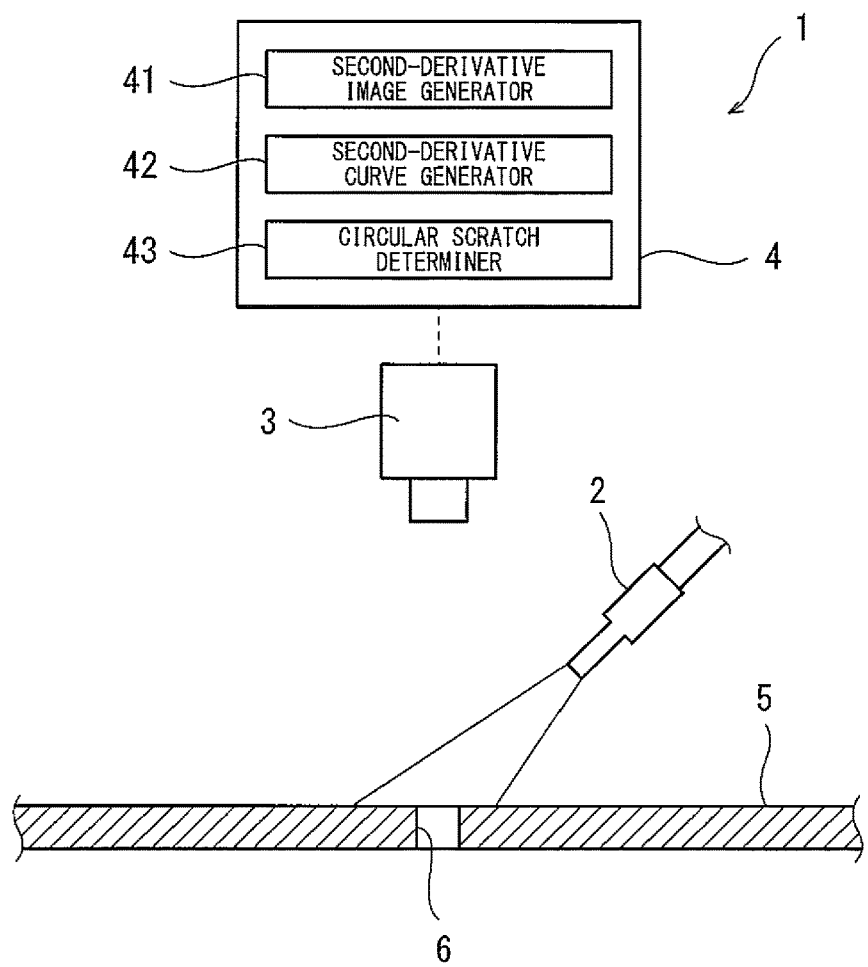
FIG. 1 shows a schematic configuration of a circular scratch inspection apparatus according to one embodiment.

FIG. 1 shows a circular scratch inspection apparatus 1 according to one embodiment. The circular scratch inspection apparatus 1 includes: a camera 3, which captures an image of a workpiece surface 5 around a hole 6 formed therein; at least one illumination device 2; and an image processor 4, which performs image processing on an actual image obtained by the camera 3.

The shape of the workpiece having the workpiece surface 5 is not particularly limited. For example, the workpiece is a plate. The hole 6 may be a through-hole extending through the workpiece, or may be a bottomed hole.

The camera 3 is disposed, for example, in a direction normal to the workpiece surface 5. The at least one illumination device 2 emits light to the workpiece surface 5 around the hole 6, such that the light that is reflected regularly on the workpiece surface 5 is not directly incident on the camera 3. For example, the optical axis direction of the illumination device 2 and the workpiece surface 5 form an angle of 25 to 60°.

In the present embodiment, the at least one illumination device 2 includes a plurality of illumination devices 2 (FIG. 1 shows only one of them), which emit light to the workpiece surface 5 around the hole 6 from different directions, respectively. For example, in the case of using two illumination devices 2, the angle between the optical axis directions of the respective illumination devices 2 is 70 to 110° when seen in the direction normal to the workpiece surface 5. It should be noted that the at least one illumination device 2 may be a ring-shaped illumination device that emits light such that the workpiece surface 5 around the hole 6 is irradiated with the light from the entire circumference.

The image processor 4 includes, for example, memories such as a ROM and RAM and a CPU. The CPU executes a program stored in the ROM. Specifically, the image processor 4 includes a second-derivative image generator 41, a second-derivative curve generator 42, and a circular scratch determiner 43.

Figure 2:
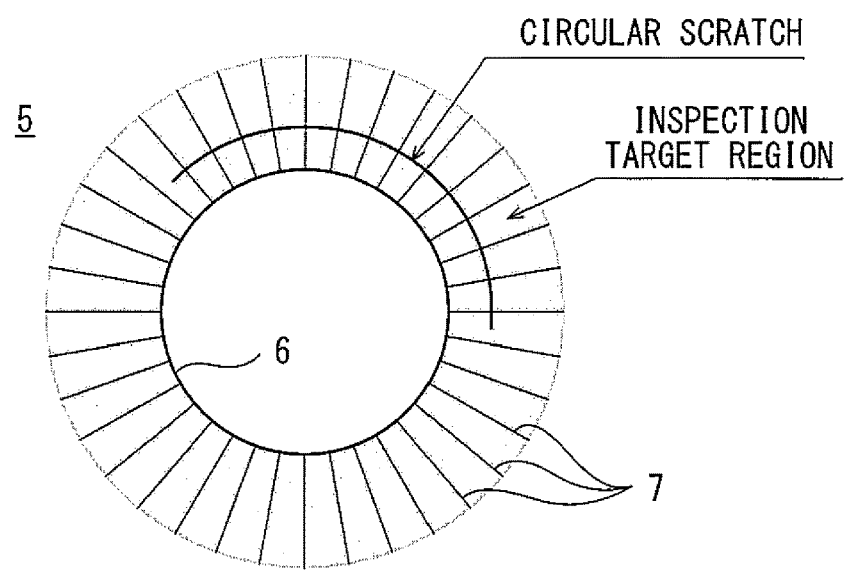
FIG. 2 is a plan view around a hole formed in a workpiece surface.
Figure 3:
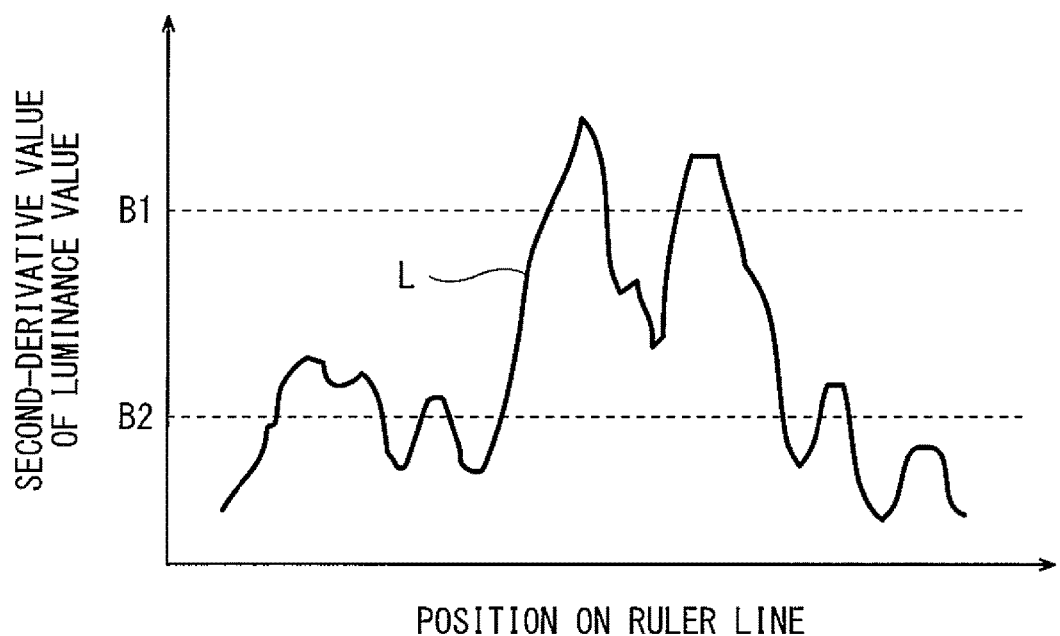
FIG. 3 shows a second-derivative curve.

The second-derivative image generator 41 generates a second-derivative image by performing secondary differentiation on luminance values in an actual image obtained by the camera 3. The second-derivative curve generator 42 generates a second-derivative curve L as shown in FIG. 3 for each of ruler lines 7, which are a plurality of imaginary lines extending radially from the center of the hole 6 as shown in FIG. 2 and which are set in an inspection target region on the workpiece surface 5. The inspection target region is a region (a grayed region in FIG. 2) surrounded by the hole 6 and a circle that is formed outside the hole 6 concentrically with the hole 6. Each second-derivative curve L indicates change in second-derivative values on the corresponding ruler line 7 in the second-derivative image. If a circular scratch is present, the circular scratch is perpendicular to at least one ruler line 7.

The number of ruler lines 7 is desirably 30 or more, and more desirably 60 or more, in order to obtain a certain number of ruler lines that cross the circular scratch. In addition, in order to reduce a time required for image processing, the number of ruler lines 7 is desirably 360 or less, and more desirably 180 or less.

The circular scratch determiner 43 counts a first reference number of times n1 for each ruler line 7, the first reference number of times n1 being the number of times the second-derivative curve L crosses a first threshold B1 on the ruler line 7. The circular scratch determiner 43 further calculates a first reference total number of times N1, which is the sum of the first reference numbers of times n1 of the plurality of ruler lines 7, and determines the presence or absence of a circular scratch by using the first reference total number of times N1.

To be more specific, the circular scratch determiner 43 counts a second reference number of times n2 for each ruler line 7, the second reference number of times n2 being the number of times the second-derivative curve L crosses a second threshold B2 on the ruler line 7, the second threshold B2 being smaller than the first threshold B1. The circular scratch determiner 43 further calculates a second reference total number of times N2, which is the sum of the second reference numbers of times n2 of the plurality of ruler lines 7.

Figure 4:
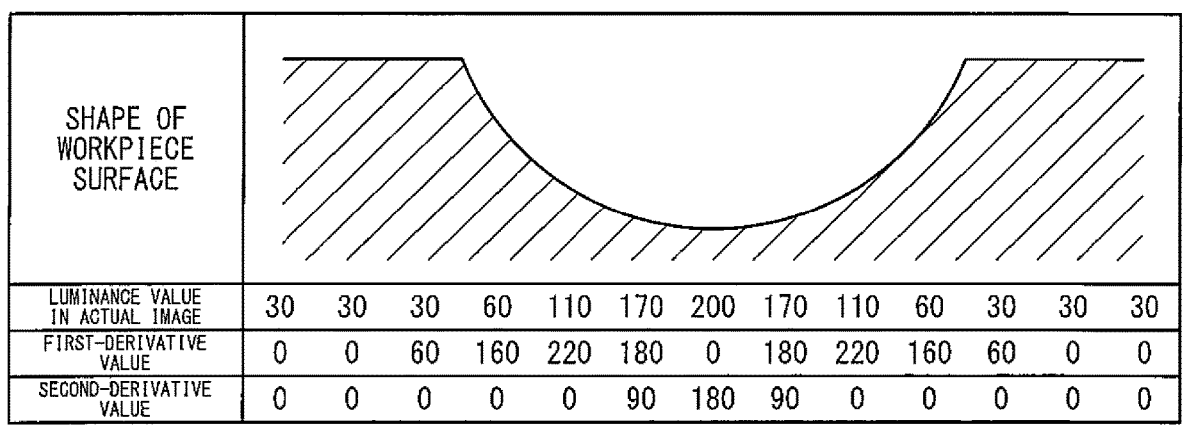
FIG. 4 shows the shape of the workpiece surface, luminance values in an actual image, first-derivative values of the luminance values, and second-derivative values of the luminance values.

As shown in FIG. 4, if a flaw is present on the workpiece surface 5, the second-derivative values of the luminance values in the actual image become great at a position where the flaw is deep. That is, by comparing the second-derivative value of each luminance value with a relatively large threshold, the presence or absence of a deep flaw can be detected. The luminance values in the actual image are affected also by, for example, surface roughness of the workpiece surface 5 and noise. Accordingly, a surface condition with no flaw can be detected by comparing the second-derivative value of each luminance value with a relatively small threshold.

In view of the above, if a value (N1/N2) obtained by dividing the first reference total number of times N1 by the second reference total number of times N2 is greater than or equal to a determination reference value V (i.e., N1/N2≥V), the circular scratch determiner 43 determines that a circular scratch is present. If the value (N1/N2) obtained by dividing the first reference total number of times N1 by the second reference total number of times N2 is less than the determination reference value V (i.e., N1/N2<V), the circular scratch determiner 43 determines that there is no circular scratch.

It should be noted that the first threshold B1 is a luminance value in the second-derivative image, the luminance value corresponding to a flaw depth that serves as a borderline between a pass and a fail in a circular scratch inspection. The second luminance value B2 is a luminance value in the second-derivative image, the luminance value serving as an index of the surface roughness of the workpiece surface 5.

Assume that there is a flaw having such a depth that the flaw will cause a fail in the circular scratch inspection. In this case, if the flaw crosses one ruler line 7, then the first reference number of times n1, i.e., the number of times the second-derivative curve L crosses the first threshold B1, is two. In this case, however, whether or not the flaw is a circular scratch cannot be determined. Although determination of a flaw as a circular scratch depends on the arc angle of the circular scratch and the number of ruler lines 7, if an arc-shaped flaw crossing three or more consecutive ruler lines 7 is to be determined as a circular scratch, then a determination that a circular scratch is present can be made when the first reference total number of times N1 is six or more.

As described above, the circular scratch inspection apparatus 1 according to the present embodiment is capable of detecting the presence or absence of a flaw on each ruler line 7 based on the first reference number of times n1, which is the number of times the second-derivative curve L crosses the first threshold B1 on the ruler line 7. Moreover, whether or not the detected flaw is a circular scratch can be determined by using the first reference total number of times N1, which is the sum of the first reference numbers of times n1 of the plurality of radially extending ruler lines 7. This makes it possible to perform an inspection to check whether or not a circular scratch is present around the hole 6 formed in the workpiece surface 5.

Further, in the present embodiment, the second reference total number of times N2, which is the sum of the second reference numbers of times n2, is used. Since the second reference number of times n2 represents a surface condition with no circular scratch, by comparing the value obtained by dividing the first reference total number of times N1 by the second reference total number of times N2 with the determination reference value V, the presence or absence of a circular scratch can be determined with reference to a surface condition with no circular scratch. Therefore, even if the intensity of the light from the illumination device 2 changes, the circular scratch inspection can be performed stably.

From the foregoing description, numerous modifications and other embodiments of the present invention are obvious to a person skilled in the art. Therefore, the foregoing description should be interpreted only as an example and is provided for the purpose of teaching the best mode for carrying out the present invention to a person skilled in the art. The structural and/or functional details may be substantially altered without departing from the spirit of the present invention.

REFERENCE SIGNS LIST 1 circular scratch inspection apparatus
2 illumination device 3 camera
4 image processor
41 second-derivative image generator
42 second-derivative curve generator
43 circular scratch determiner
5 workpiece surface
6 hole
7 ruler line

What is claimed is:

1. A circular scratch inspection apparatus comprising:
a camera that captures an image of a workpiece surface around a hole formed therein;
at least one illumination device that emits light to the workpiece surface around the hole, such that the light that is reflected regularly on the workpiece surface is not directly incident on the camera; and
an image processor that performs image processing on an actual image obtained by the camera, wherein
the image processor includes:
a second-derivative image generator that generates a second-derivative image by performing secondary differentiation on luminance values in the actual image;
a second-derivative curve generator that generates a second-derivative curve for each of a plurality of ruler lines, which extend radially from a center of the hole and which are set in an inspection target region on the workpiece surface, the second-derivative curve indicating change in second-derivative values on each ruler line in the second-derivative image; and
a circular scratch determiner that counts a first reference number of times for each ruler line, the first reference number of times being the number of times the second-derivative curve crosses a first threshold on the ruler line, calculates a first reference total number of times, which is a sum of the first reference number of times of each of the plurality of ruler lines, and determines presence or absence of a circular scratch by using the first reference total number of times.

2. The circular scratch inspection apparatus according to claim 1, wherein
the circular scratch determiner:
counts a second reference number of times for each ruler line, the second reference number of times being the number of times the second-derivative curve crosses a second threshold on the ruler line, the second threshold being smaller than the first threshold;
calculates a second reference total number of times, which is a sum of the second reference numbers of times of the plurality of ruler lines; and
determines that the circular scratch is present if a value obtained by dividing the first reference total number of times by the second reference total number of times is greater than or equal to a determination reference value, and determines that there is no circular scratch if the value obtained by dividing the first reference total number of times by the second reference total number of times is less than the determination reference value.

3. The circular scratch inspection apparatus according to claim 1, wherein
the at least one illumination device comprises a plurality of illumination devices, which emit light to the workpiece surface around the hole from different directions, respectively.

4. The circular scratch inspection apparatus according to claim 2, wherein
the at least one illumination device comprises a plurality of illumination devices, which emit light to the workpiece surface around the hole from different directions, respectively.

* * * * *